United States Patent
Maiti

(10) Patent No.: US 10,513,552 B2
(45) Date of Patent: *Dec. 24, 2019

(54) USE OF POLYCLONAL ANTIBODIES AGAINST CLOSTRIDIUM DIFFICILE FOR TREATMENT OF INFLAMMATORY BOWEL DISEASE

(71) Applicant: IMMUNIMED INC., Winnipeg (CA)

(72) Inventor: Pradip K. Maiti, Winnipeg (CA)

(73) Assignee: IMMUNIMED INC., Winnipeg, Manitoba (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/845,214

(22) Filed: Dec. 18, 2017

(65) Prior Publication Data

US 2018/0362618 A1  Dec. 20, 2018

Related U.S. Application Data

(63) Continuation-in-part of application No. 14/745,588, filed on Jun. 22, 2015, now Pat. No. 9,873,732.

(60) Provisional application No. 62/015,339, filed on Jun. 20, 2014.

(51) Int. Cl.

| C07K 16/02 | (2006.01) |
|---|---|
| A61K 9/00 | (2006.01) |
| C07K 16/40 | (2006.01) |
| A61K 39/00 | (2006.01) |
| A61P 1/00 | (2006.01) |
| C07K 16/12 | (2006.01) |
| A61P 31/04 | (2006.01) |

(52) U.S. Cl.
CPC ............ *C07K 16/02* (2013.01); *A61K 9/0053* (2013.01); *A61K 9/0095* (2013.01); *A61P 1/00* (2018.01); *A61P 31/04* (2018.01); *C07K 16/1282* (2013.01); *C07K 16/40* (2013.01); *A61K 2039/542* (2013.01); *C07K 2317/11* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| 6,969,520 | B2 | 11/2005 | Thomas | |
|---|---|---|---|---|
| 7,785,818 | B2* | 8/2010 | Boone | G01N 33/56972 435/7.1 |
| 7,820,171 | B2* | 10/2010 | Maiti | C07K 16/12 424/130.1 |
| 8,257,709 | B2 | 9/2012 | Ambrosin et al. | |
| 8,921,529 | B2 | 12/2014 | Shone et al. | |
| 8,986,697 | B2 | 3/2015 | Ma | |
| 9,139,625 | B2 | 9/2015 | Cutting et al. | |
| 9,873,732 | B2* | 1/2018 | Maiti | A61K 39/08 |
| 10,196,453 | B2* | 2/2019 | Cowardin | C07K 16/2896 |
| 2007/0071795 | A1 | 3/2007 | Pradip et al. | |
| 2012/0276059 | A1 | 11/2012 | Boone | |
| 2013/0004561 | A1 | 1/2013 | Shone | |
| 2014/0127215 | A1* | 5/2014 | Berry | A61K 39/08 424/139.1 |
| 2015/0017181 | A1 | 1/2015 | Kelly | |
| 2015/0368320 | A1* | 12/2015 | Maiti | A61K 39/08 424/158.1 |
| 2016/0083457 | A1* | 3/2016 | Lyras | C07K 16/1282 424/157.1 |
| 2017/0334994 | A1* | 11/2017 | Cowardin | C07K 16/2896 |
| 2018/0022784 | A1* | 1/2018 | Gaudreau | C07K 14/33 424/239.1 |
| 2018/0155410 | A1* | 6/2018 | Borody | A61K 35/74 |
| 2018/0256697 | A1* | 9/2018 | Sun | A61K 39/08 |
| 2018/0362618 | A1* | 12/2018 | Maiti | C07K 16/02 |

FOREIGN PATENT DOCUMENTS

| CA | 2560283 | | 3/2007 | |
|---|---|---|---|---|
| CA | 2895217 | A1 * | 12/2015 | ............ A61K 39/08 |
| WO | 9413264 | | 6/1994 | |
| WO | 9902188 | | 1/1999 | |
| WO | WO-9902188 | A1 * | 1/1999 | ............ C07K 16/02 |
| WO | 2014169344 | | 10/2014 | |

OTHER PUBLICATIONS

Wang et al, Infection and Immunity, Nov. 2018, 86/11:e00489-18, 10 pages. (Year: 2018).*
Tlan et al, Vaccine 30, 2012 pp. 4249-4258. available online Apr. 23, 2012 (Year: 2012).*
Warn et al, Antimicrobial Agents and Chemotherapy, Nov. 2016, 60/11:6471-6482. (Year: 2016).*
Foglia et al, Vaccine 30, 2012, pp. 4307-7309. (Year: 2012).*
Maynard-Smith et al, Vaccine 32, 2014, pp. 700-705. available online: Dec. 14 13 (Year: 2014).*
Sun et al, Infection and Immunity, Jul. 2011, 79/7:2856-2864. published ahead of print on May 16, 2011 (Year: 2011).*
Tian et al, Vaccine 35, 2017, pp. 4079-4087. available online Jun. 29, 2017 (Year: 2017).*

(Continued)

*Primary Examiner* — Nita M. Minnifield
(74) *Attorney, Agent, or Firm* — Michael R. Williams; Ryan W. Dupuis; Ade & Company Inc.

(57) ABSTRACT

The present invention provides a polyclonal antibody composition prepared from eggs of hens immunized with virulent antigens of *Clostridium difficile* for use in the treatment and prevention of *C. difficile* infections in subjects with Inflammatory Bowel Disease including Ulcerative colitis and Crohn's disease. Respective groups of hens are immunized with Toxin A or Toxin B of *Clostridium difficile* or a *Clostridium difficile* spore preparation. The polyclonal antibodies are recovered from eggs pooled from the immunized hens and the resulting antibody-egg powder is administered orally in a therapeutically effective amount to individuals infected with or suspected of being infected with *C. difficile*.

18 Claims, 9 Drawing Sheets

(56) References Cited

OTHER PUBLICATIONS

Figure 1:
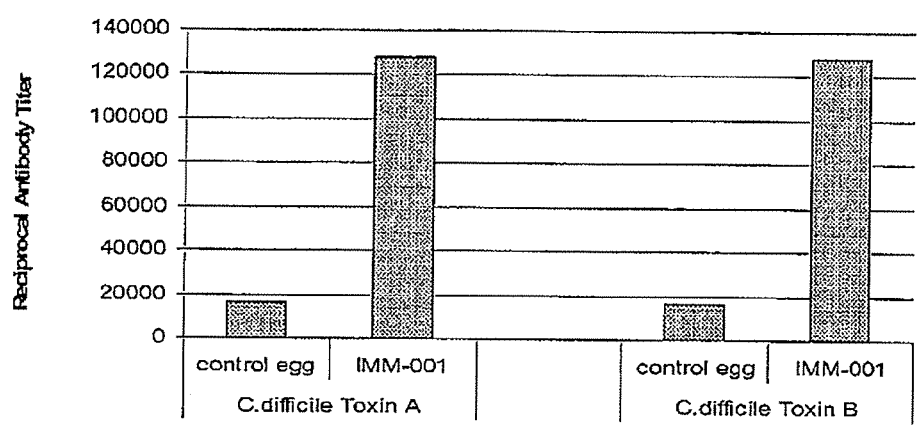

Kink J A et al: "Antibodies to Recombinant Clostridium Difficile Toxins A and B are Effective Treatment and Prevent Relapse of C. Difficile—Associated Disease in a Hamster Model of Infection", Infection and Immunity, American Society for Microbiology, US, vol. 66, No. 5, May 1, 1998, pp. 2018-2025, ISSN: 0019-9567.

Min S Song et al: "Growth Inhibition of Clostridium Perfringens Vegetative Cells and Spores using Chicken Immunoglobulin Y", Journal of Food Safety 2009 Correspondence Address, Hoon H. Sunwood, CJ Foods R&D, CJ Coporation 636, Guro-Dong, Guro-Gu, Seoul, South Korea., vol. 29, No. 4, Jan. 1, 2009, pp. 211-250.

* cited by examiner

FIGURE 6

USE OF POLYCLONAL ANTIBODIES AGAINST CLOSTRIDIUM DIFFICILE FOR TREATMENT OF INFLAMMATORY BOWEL DISEASE

PRIOR APPLICATION INFORMATION

The instant application is a continuation-in-part application of U.S. patent application Ser. No. 14/745,588, filed Jun. 22, 2015, entitled "Polyclonal Antibodies Against *Clostridium difficile* and Uses Thereof", which claimed the benefit of U.S. Provisional Patent Application Ser. No. 62/015,339, filed Jun. 20, 2014, entitled 'Antibodies against *Clostridium difficile* and uses thereof', the contents of both of which are incorporated herein by reference.

FIELD OF THE INVENTION

The invention relates generally to the field of compositions for the treatment of Inflammatory Bowel Disease and associated diseases such as ulcerative colitis and Crohn's disease. More specifically, the invention relates to a polyclonal antibody composition prepared from eggs of immunized hens. Yet more specifically, the invention relates to a polyclonal antibody composition prepared from eggs of hens immunized with Toxin A and Toxin B of *Clostridium difficile* and a *Clostridium difficile* spore preparation that is administered orally to patients for example humans to treat *Clostridium difficile* infections and the symptoms associated therewith.

BACKGROUND OF THE INVENTION

*Clostridium difficile* (*C. difficile* or *C. diff*) is a Gram-positive, spore-forming bacterium that causes hospital-acquired as well as community-acquired enteric infections. Infections can be asymptomatic but generally lead to *C. diff*-associated diarrhea, pseudomembranous colitis, colitis and death (Halsey, J. 2008, *Am J Health Syst Pharm* 65(8):705-15; Lessa, F. C. et al. 2012, *Clin Infect Dis.* 55(Suppl 2): S65S70).

*C. difficile* infection is often but not always induced by antibiotic disruption of the colonic flora through the use of antibiotics such as clindamycin, cephalosporins, and fluoroquinolones. This perturbation in the colonic microenvironment, along with exposure to *C. difficile* spores, leads to mucosal *C. difficile* colonization. This colonization may result from the presence of a pre-existing antibiotic resistant *C. difficile* or concomitant exposure to *C. difficile* spores, particularly in hospitals. Approximately one-third of all patients that become colonized develop CDAD, which can result in severe diarrhea, perforation of the colon, colectomy and death. CDAD results from the acquisition and proliferation of *C. difficile* in the gut, where *C. difficile* bacteria produce toxin A and toxin B, two important virulence factors of CDAD. Toxins A and B of *C. difficile* show considerable sequence and structural homology. Both have a C-terminal receptor-binding domain containing multiple repeating sequences, a central hydrophobic domain and an N-terminal glucosyltransferase domain. The receptor-binding domain mediates binding of the toxins to intestinal epithelial cells via host receptors that remain poorly defined in humans. Following internalization via an endosomal pathway, the central hydrophobic domain inserts into the membrane of the endosome. The acidic pH of the endosome triggers pore formation and translocation of the amino-terminal domains of the toxins into the cytosol. Glucosylation of the cytosolic target Rho GTPases leads to disruption of the cytoskeleton and cell death. Toxins A and B demonstrate different pathological profiles and have potential synergy in causing disease.

Current treatment for *C. difficile* infection (CDI) is the use of certain antibiotics, such as for example but by no means limited to Metronidazole, Vancomycin, and Fidaxomycin, either alone or in combination. However, efficacies of these antibiotics are limited by incomplete response rates with increasing re-infection and recurrence rates. The antibiotic therapy does not provide complete protection to all patients; as a result, 25-40% of patients suffer from *C. difficile* recurrent infections (Figueroa, I. et al 2012, *Clin Infect Dis.* 55 Suppl 2:S104-9).

Of great concern, a sharp rise in the rate of *C. difficile* infection in patients with inflammatory bowel disease (IBD) in recent years. (Rodemann J F et al, 2007; Odes, S L et al. 2011, Hanada et al., 2017). Prior antibiotic use is not detected in 40% of *C. difficile* outbreaks in IBD patients and many infections are in fact community-acquired as opposed to hospital-acquired *C. difficile* infections.

Inflammatory Bowel Disease (IBD) is an umbrella term used to describe disorders that involve chronic inflammation of the digestive tract. IBD is generally attributed to an inappropriate immunologic response to otherwise commensal flora in a genetically susceptible host (Hanada et al., 2017). Symptoms of IBD most commonly include fever, vomiting, diarrhea, bloody stool, abdominal pain and weight loss. Types of IBD include ulcerative colitis and Crohn's disease.

Ulcerative colitis causes long-lasting inflammation and sores (ulcers) in the innermost lining of the large intestine (colon) and rectum. UC is usually characterized by inflammation of the colon and the rectum.

Crohn's disease is characterized by inflammation of the lining of the digestive tract, which often spreads deep into affected tissues. CD commonly manifests as inflammation of the small intestine, but can affect other parts of the body as well.

UC and CD are commonly regarded as autoimmune diseases, with evidence suggesting they are the result of misdirected immune response. The etiology of IBD appears to involve complex interactions of genetic predisposition, environmental factors, disruption of the intestinal microbiome and an overly aggressive immune response. In addition, evidence linking the ability of intestinal epithelial cells to modify the mucosal immune response, may suggest an invasive bacterial pathway. Imbalance in intestinal microbiota of gut friendly bacteria destroyed by antibiotics as well as opportunistic pathogens are implicating factors as well (U.S. Pat. No. 9,694,348). Specifically, patients with IBD have been reported to have an abnormal gut microbiota. Whether this altered flora is the cause or the result of chronic inflammation remains unclear.

Patients with IBD have a higher incidence of CDI than persons without IBD. Additionally, IBD patients with CDI have poorer outcomes, including longer length of hospital stay, higher colectomy rates and increased mortality (Hanada et al., 2017).

As such, IDB is assumed to predispose individuals for CDI. Reductions in gut microbial diversity have been identified in IBD patients. Although a causative role for this dysbiosis in the development of IBD has not been well established, it is plausible that dysbiosis may play a role in increasing CDI in IBD patients (D'aoust et al., 2017). The overlap in symptomatology between CDI and IBD flare or relapse complicates the diagnosis of CDI in IBD patients.

CDI and acute inflammatory colitis are clinically indistinguishable (D'aoust et al., 2017), both being characterized by diarrhea, abdominal pain, fever and leukocytosis (Nitzan et al., 2013). Despite this, CDI is typically treated with administration of antibiotics and/or fecal microbiota transplantation while IBD is primarily treated with corticosteroids or other immunosuppressive therapies. In fact, one recommended treatment for CDI overlaying IBD is antibiotic therapy followed shortly thereafter with immunosuppressive therapy (D'aoust et al., 2017). Others suggest that immunosuppression be maintained but not escalated in instances where CDI is superimposed over IBD (Nitzan et al., 2013).

In one study, of 124,570 hospital discharges, 2.3% were diagnosed as having both *C. difficile* and IBD, 36% *C. difficile* alone and 62% IBD alone. Multivariate analysis of patients in the *C. difficile*-IBD group had four times greater mortality than patients admitted for IBD alone (OR 4.7) or *C. difficile* alone (OR 2.2) (Saidel-Odes et al., 2011, Annals of Gastroenterology 24: 263-270).

Despite this, the prior art remains uncertain as to whether *C. difficile* is a cause of IBD or a consequence of the inflammatory state in the intestinal environment (Nitzan et al., 2013). Specifically, it is hypothesized that the association between IBD and *C. difficile* may be due to different factors, such as drugs that are used for the treatment of IBD that might alter the intestinal flora or promote colonization, altered immune and nutritional status, frequent hospitalization and even genetic predisposition.

Detection of *C. difficile* in IBD patients is not easy, as there is no specific dependable clinical picture or stool characteristic. In patients with IBD, the chance of *C. difficile* infection is greater, although why this occurs is not understood. In one study, qPCR detected *C. difficile* in 34 of 37 patients with UC who had not been exposed to antibiotics, whereas the toxin test for *C. difficile* was positive in only 8 of the 37 patients (Saidel-Odes et al., 2011).

Furthermore, there are no studies evaluating treatment of the asymptomatic carriage of *C. difficile*. The prior art is unclear if treatment of asymptomatic *C. difficile* carriers would have any impact on IBD disease or the development of symptomatic CDI; however, in the general population, carriage of *C. difficile* in the absence of symptoms is considered to carry a protective effect against future symptomatic CDI, although this protective effect has not been studied in the IBD population (D'aoust, 2017).

*C. difficile* infection now poses a serious problem in IBD patients. There is an alarming increase in morbidity, mortality, need for surgery, and health care cost resulting from *C. difficile* colitis occurring in IBD patients compared with non-infected IBD subjects; therefore, *C. difficile* now presents an important public health issue for gastroenterologists.

In IBD patients, the early identification and treatment of *C. difficile* superinfection is clearly important to avoid serious outcomes. Given the changing epidemiology of the *C. difficile* infection the most important step is to treat *C. difficile* infection in order to avoid potential complication in IBD patients.

SUMMARY OF THE INVENTION

The present invention provides antibody compositions comprising of egg-derived antibodies and methods for the treatment and prevention of Inflammatory Bowel Disease in human and other animals.

In one aspect, the invention provides compositions comprising antibodies developed against and/or targeting *C. difficile* virulent antigens.

In some embodiments, the antibodies target *C. difficile* toxins A, toxin B, spores and/or other virulent antigens responsible for the pathogenesis of CDI. In some embodiments, the antibodies target *C. difficile* toxin A, toxin B, or binary toxin. In some embodiments, the antibodies target *C. difficile* spores. In some embodiments, the antibodies target other virulent antigens responsible for the pathogenesis of CDI.

In some embodiments, the antibodies are polyclonal antibodies. In some embodiments, the polyclonal antibody preparation is referred to as IM-01.

In some embodiments, the polyclonal antibodies are generated by immunizing animals, for example, birds with the pathogen of interest. In some embodiments, the polyclonal antibodies are generated by immunizing animals with a virulent antigen of the pathogen. In some other embodiments, the polyclonal antibodies are generated by immunizing animals with an inactivated or attenuated strain of the pathogen. In some embodiments, the polyclonal antibodies are produced in the form of eggs from the birds. In some embodiments, the polyclonal antibodies are purified, recovered or isolated from the eggs. In some embodiment, the immunized birds are chickens or hens.

In some embodiments, the polyclonal antibodies are used in the preparation of a composition suitable for oral consumption.

In some embodiments, the polyclonal antibodies are used in the preparation of a pharmaceutical composition for the treatment of Inflammatory Bowel Disease, for example, Ulcerative Colitis or Crohn's Disease.

In one aspect, the invention provides egg-derived pathogen-specific polyclonal antibody therapeutics.

In another aspect, the invention provides a method of treating a subject suspected of having or diagnosed with Inflammatory Bowel Disease, the method comprising administering to the subject an effective amount of the compositions or the polyclonal antibodies described herein.

In another aspect, the invention provides a method of preventing a subject from developing an Inflammatory Bowel Disease flare or relapse, the method comprising administering to the subject the compositions or the antibodies described herein. For example, the subject may be an individual who is known to have or who has had Inflammatory Bowel Disease previously for example in the recent past or who is experiencing symptoms consistent with an Inflammatory Bowel Disease flare, as discussed herein and as known in the art. Specifically, as discussed herein, *C. difficile* is known to be linked to flares of IBD. Accordingly, treatment or reduction or elimination of *C. difficile* will in turn accomplish at least one of the following: eliminate flares of IBD, reduce severity or duration of flares of IBD, and/or increase period of time between flares compared to an individual of similar age and condition who also has IBD and an associated *C. difficile* infection but does not receive polyclonal antibodies against *C. difficile*, as discussed herein.

In some embodiments, the subject is a human. In other embodiments, the subject is a non-human animal.

In some embodiments, the method comprises administering the composition or the polyclonal antibodies to the subject orally.

In one aspect, the invention provides a method for generating the antibodies of the invention. In some embodiments, the method comprises immunizing animals for example birds with the pathogen of interest, a virulent antigen of the pathogen, or an inactivated or attenuated strain of the pathogen. In some embodiments, the method further comprises harvesting eggs from the birds. In some embodiments, the method further comprises purifying the antibodies from the eggs. In some embodiment, the immunized birds are chickens or hens.

According to a first aspect of the invention, there is provided a method of preparing a polyclonal antibody composition for treating or preventing or prophylactically treating a *Clostridium difficile* infection associated with Inflammatory Bowel Disease comprising:

a) immunizing a first group of egg-laying hens with an antigen prepared from *Clostridium difficile* Toxin A;

b) immunizing a second group of egg-laying hens with an antigen prepared from *Clostridium difficile* Toxin B;

c) immunizing a third group of egg-laying hens with an antigen prepared from *Clostridium difficile* spores;

d) collecting eggs laid by said first group, said second group and said third group; and e) recovering polyclonal antibodies from said collected eggs.

The antigens may be administered to the hens in combination with an adjuvant. In some embodiments the adjuvant is Montanide-ISA-70.

In some embodiments, the polyclonal antibodies are recovered from the collected eggs by freeze-drying the eggs or by spray-drying.

Preferably, the polyclonal antibody composition has a reciprocal titer of <128,000.

According to another aspect of the invention, there is provided the use of the polyclonal antibody composition described above to treat or prevent or prophylactically treat Inflammatory Bowel Disease, as discussed herein.

In one aspect of the invention, there is provided a method for treating or preventing or prophylactically treating Inflammatory Bowel Disease or a flare of Inflammatory Bowel disease associated with *C. difficile* comprising administering to an individual in need of such treatment an effective amount of a polyclonal antibody composition, said polyclonal antibody composition being prepared by a method comprising:

a) Immunizing a first group of egg-laying hens with an antigen prepared from *Clostridium difficile* Toxin A;

b) immunizing a second group of egg-laying hens with an antigen prepared from *Clostridium difficile* Toxin B;

c) immunizing a third group of egg-laying hens with an antigen prepared from *Clostridium difficile* spores;

d) collecting eggs laid by said first group, said second group and said third group;

e) recovering polyclonal antibodies from said collected eggs; and f) administering an effective amount of the polyclonal antibodies to an individual in need of such treatment.

As discussed herein, the flare of Inflammatory Bowel Disease may be treated or prophylactically treated or prevented or delayed by administering to an individual who has had an Inflammatory Bowel Disease episode previously and who is known to be or who is suspected of being a carrier of *C. difficile* an effective amount of the polyclonal antibody preparation prepared as described above. As discussed herein, in some embodiments of the invention, the polyclonal antibodies are administered in the absence of co-administration of corticosteroids or other immunosuppressive agents, as discussed herein.

In another aspect of the invention, there is provided a polyclonal antibody composition for treating or preventing or prophylactically treating Inflammatory Bowel Disease or a flare of Inflammatory Bowel Disease associated with a *C. difficile* infection or associated with *C. difficile* characterized in that said polyclonal antibody composition being prepared by a method comprising:

a) immunizing a first group of egg-laying hens with an antigen prepared from *Clostridium difficile* Toxin A;

b) immunizing a second group of egg-laying hens with an antigen prepared from *Clostridium difficile* Toxin B;

c) immunizing a third group of egg-laying hens with an antigen prepared from *Clostridium difficile* spores;

d) collecting eggs laid by said first group, said second group and said third group; and e) recovering polyclonal antibodies from said collected eggs.

According to a further aspect of the invention, there is provided use of a polyclonal antibody composition for treating or preventing or prophylactically treating Inflammatory Bowel Disease or a flare of Inflammatory Bowel Disease associated with *C. difficile* characterized in that said polyclonal antibody composition is prepared by a method comprising:

a) immunizing a first group of egg-laying hens with an antigen prepared from *Clostridium difficile* Toxin A;

b) immunizing a second group of egg-laying hens with an antigen prepared from *Clostridium difficile* Toxin B;

c) immunizing a third group of egg-laying hens with an antigen prepared from *Clostridium difficile* spores;

d) collecting eggs laid by said first group, said second group and said third group; and e) recovering polyclonal antibodies from said collected eggs.

BRIEF DESCRIPTION OF THE DRAWINGS

FIG. 1. IM-01 Antibody Reactivity to *C. difficile* Toxin A and *C. difficile* Toxin B. ELISA plates were coated with *C. difficile* toxin A and *C. difficile* toxin B. Both controls (egg powder from chickens prior to immunizations with *C. difficile* antigens) and IM-01 polyclonal antibodies were diluted to 1:140,000, and incubated with toxins on the plates to determine binding activity. IM-01 showed strong positive reactivity against both *C. difficile* Toxin A and Toxin B at a dilution of 1:128,000, when control egg powder did not show any reactivity to any of the toxins.

FIG. 2. Reactivity of IM-01 antibodies to *C. difficile* toxins produced in culture supernatant by genetically diverse *C. difficile* strains. IM-01 polyclonal antibodies showed strong reactivity against toxins produced by all seven clinical isolates of *C. difficile* with four different ribotype, 002, 003, 019 and 027. However, the reactivity was strongest with 1/10 dilution and weakest with the 1/500 dilution of culture supernatant. The Figure demonstrates that clinical isolates of *C. difficile* produced variable amounts of toxins in vitro in the culture supernatants. IM-01 antibodies exhibited strong reactivity and the reactivity determined to be toxin-concentration dependent.

FIG. 3. IM-01 Neutralizing cytopathic effect of *C. difficile* Toxin A and Toxin B mediated cytotoxicity using cell-based assay with IMR-90 cells in vitro. Well established, IMR-90, Human lung fibroblast cell line, were incubated with *C. difficile* toxin A+toxin B in different concentrations. Cytopathic effects (CPE) were determined by visual inspection of rounded cells under microscope. A CPE score 4, =100% cell cytotoxicity, and CPE score 0=0% cytotoxicity or 100% neutralization. Results shown in figure that IM-01 polyclonal antibodies are able to neutralize 100% cytotoxicity-mediated by toxin A and toxin B in IM-01 antibody dose dependent manner, IM-01 showed toxin neutralization at 1:162 dilutions, when Goat polyclonal antibodies used as positive control showed neutralization at 1:54 dilution.

Figure 4:
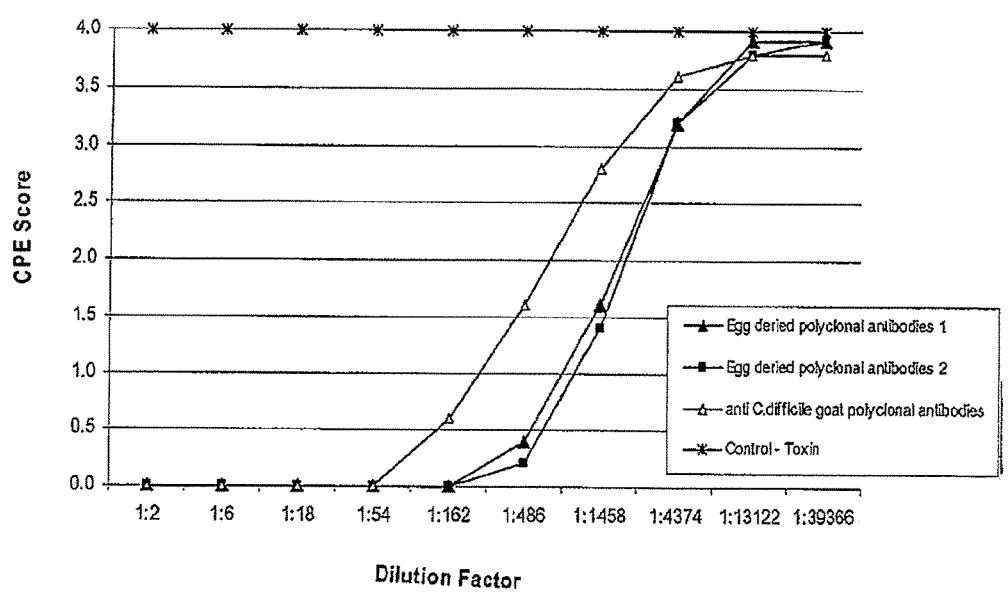

FIG. 4. Neutralization of *C. difficile* Toxin A and B cytotoxicity in IMR-90 cells by Goat polyclonal antibodies and Egg-derived polyclonal antibodies IM-01.

The cytopathic effects were determined by observing the percent of cells that had become rounded in presence of toxins. When there is no cytopathic effect, i.e. cells that had not become rounded with toxin in presence of antibodies, toxin was considered neutralized. IM-01 showed toxin neutralization at 1:162 dilutions, when Goat polyclonal antibodies used as positive control showed neutralization at 1:54 dilution.

Figure 5:
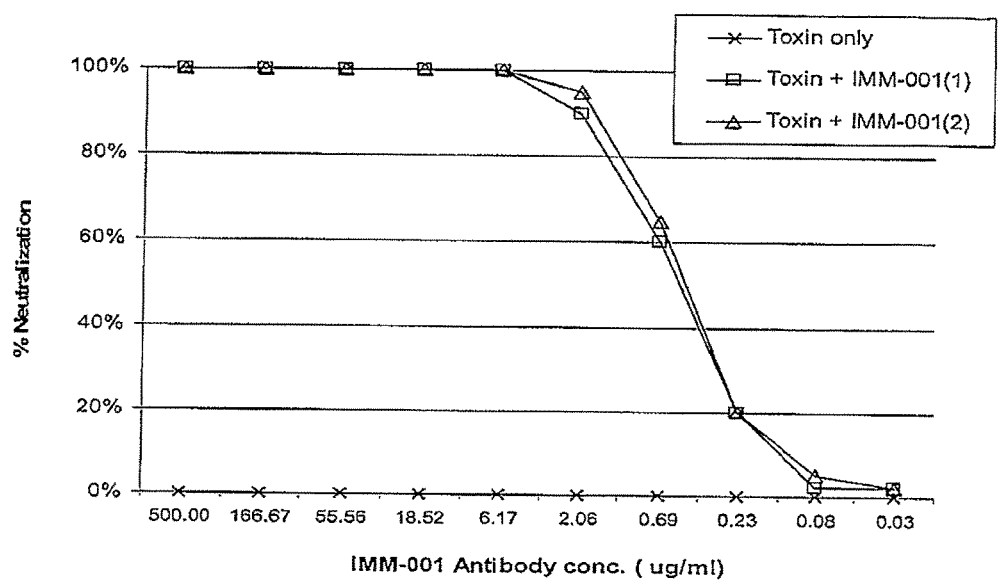

FIG. 5. Toxin neutralization ability of IM-01 polyclonal antibodies in vitro. No toxin neutralization activity was detected when the cells were incubated with toxin alone. In contrast, maximum neutralization activity (100%) was achieved when the toxin was mixed with IM-01 antibody concentration at 6.17 μg/mL or higher. However, the toxin neutralization ability was diminished to zero when the lowest amount (0.06 μg/mL) of IM-01 antibodies was added to the toxin.

Figure demonstrated that IM-01 polyclonal antibodies are capable of neutralizing cytopathic effects of *C. difficile* toxins on IMR-90 cells in vitro and the efficacy is IM-01 polyclonal antibody concentration-dependent.

Figure 6:
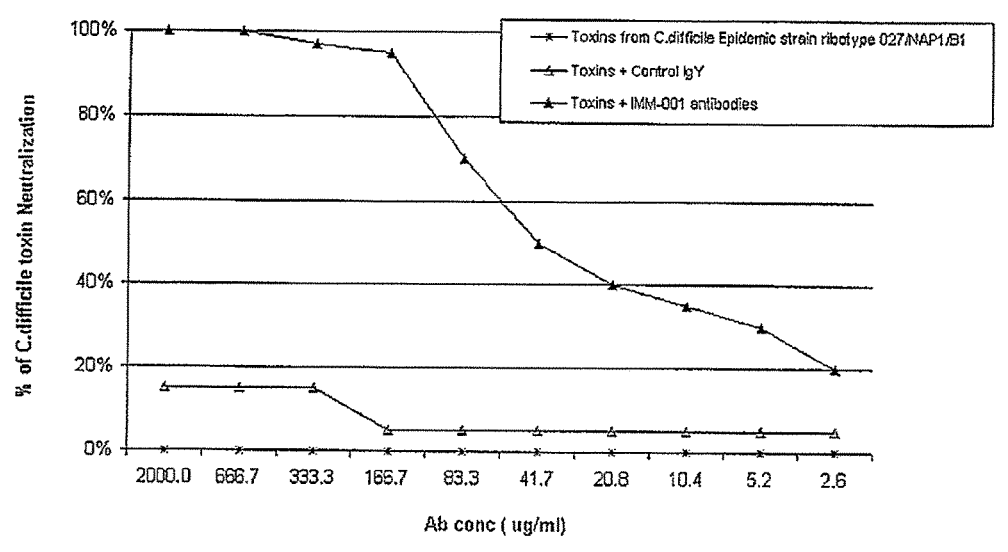

FIG. 6. Toxin neutralization ability of IM-01 to toxins produced by hypervirulent *C. difficile* strain in cell-based assay using T-84 cells.

The Figure demonstrates that toxin A & B alone demonstrated 100% cytopathic effect with no toxin neutralization on T-84 cells. *C. difficile* toxin+control egg powder showed 85-90% cytopathic effect with 10-15% toxin neutralization on T-84 cells. In contrast, toxin A & B+IM-01 antibody showed 0% cytopathic effect with 100% toxin neutralization, but the toxin neutralization ability of IM-01 antibody is determined to be antibody dose-dependent.

Figure 7:
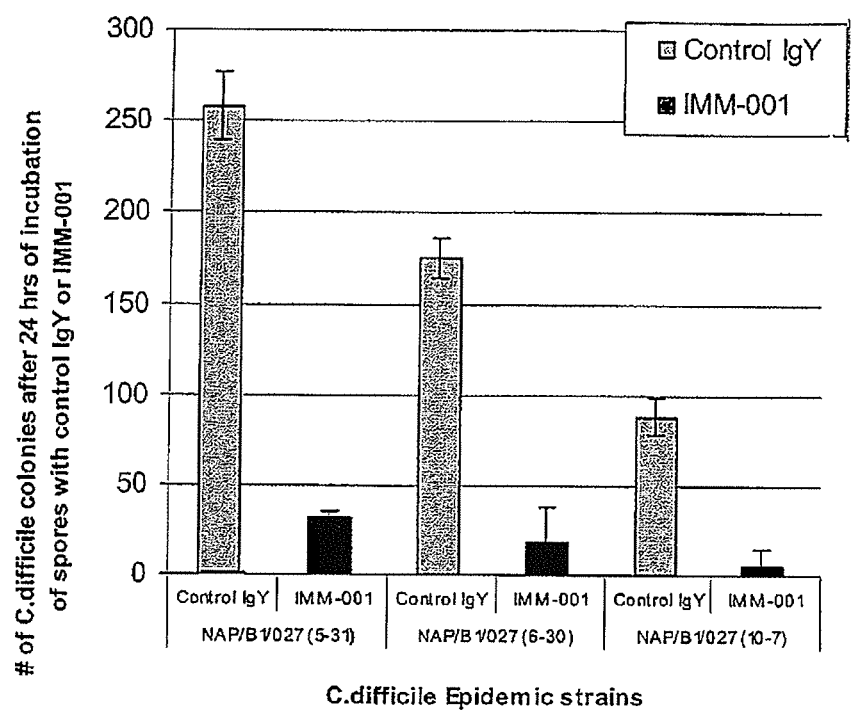

FIG. 7. Effect of IM-01 antibodies on growth inhibition of hypervirulent *C. difficile* strains. As shown in the Figure, that the 90-260 colonies were detected after incubation of a fixed number of *C. difficile* spores with control egg powder from non-vaccinated chicken. In contrast, only 5-20 colonies were detected following incubation of the same number of spores of *C. difficile* hypervirulent strains with IM-01 antibodies.

Figure 8:
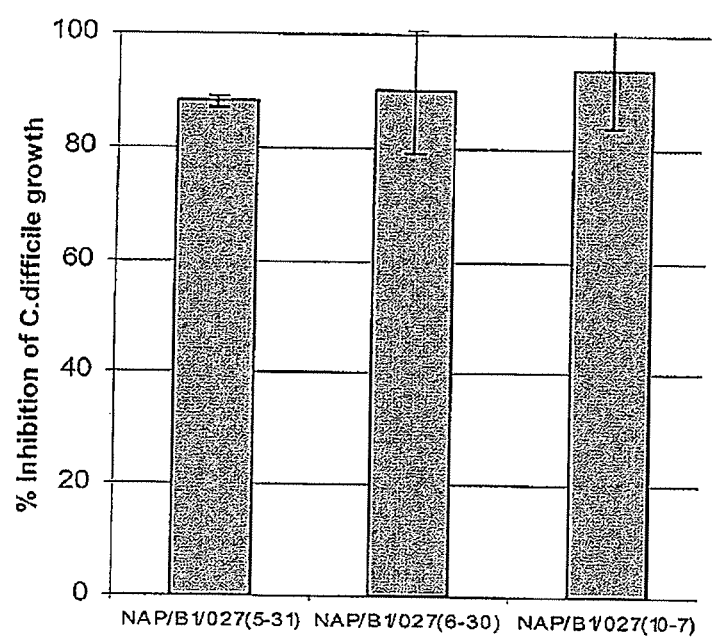

FIG. 8. Effect of IM-01 antibodies in vitro on inhibition of growth of hypervirulent *C. difficile* strains.

The Figure demonstrated that IM-01 antibodies inhibited >80% growth of all three *C. difficile* isolates of hypervirulent NAP/B1/027 strains.

Figure 9:
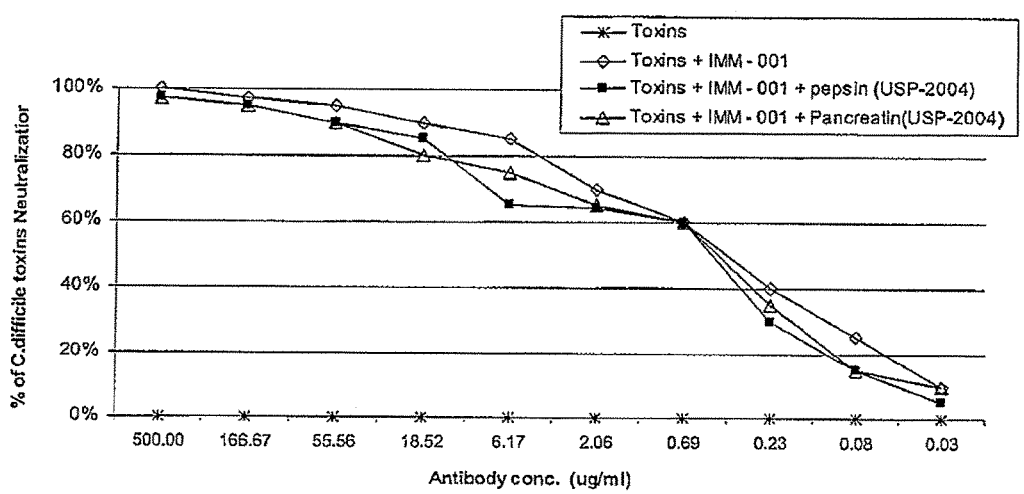

FIG. 9. Measurement of Gastric stability of IM-01 formulation.

It has been demonstrated that toxin-neutralization ability of IM-01 antibodies in its current formulation, as measured by cytotoxicity assay, is protected from digestive enzymes under simulated gastric and intestinal conditions.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Some aspects of the invention, including but not limited to some methods for generating the polyclonal antibodies of the invention, are disclosed in U.S. Pat. No. 7,713,527 (Filed: Sep. 18, 2006; Issued: May 11, 2010), U.S. Pat. No. 7,820,171 (Filed: Apr. 14, 2008; Issued: Oct. 16, 2010), Canadian Patent No. CA 2560283 (Filed: Sep. 18, 2006, Issued: Nov. 19, 2013), and Canadian Patent No. CA 2629790 (Filed: Apr. 14, 2008, Issued: Nov. 12, 2013), all of which are incorporated herein by reference.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', F(ab')2, scFv, dsFv, ds-scFv, dimers, minibodies, diabodies, and multimers thereof and biospecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, biospecific antibody fragments and other fragments can also be synthesized by recombinant techniques.

Described herein is a polyclonal antibody composition prepared from eggs of *C. difficile* virulent antigens immunized hens is used to treat or prevent or prophylactically treat Inflammatory Bowel Disease, or in some embodiments, a flare of Inflammatory Bowel Disease associated with *C. difficile*. As discussed below, respective groups of hens are immunized with Toxin A or Toxin B of *Clostridium difficile* or a *Clostridium difficile* spore preparation. The polyclonal antibodies are recovered, isolated or purified from eggs pooled from the immunized hens and the resulting powder is administered in a therapeutically effective amount to individuals infected with or suspected of being infected with *C. difficile*. Specifically, the polyclonal antibody composition comprises antibodies which will bind to *C. difficile* virulence factors and spores and will also block pathogenic effects of *C. difficile* Toxin A and Toxin B.

As discussed above, *C. difficile* produces an infectious colitis, which, when superimposed with an idiopathic colitis in an individual, creates a synergy that can make both conditions worse. IBD is destabilized by *C. difficile* infection, and as such the prior art teaches controlling *C. difficile* while addressing the flare of the IBD colitis, which has been induced by the infection (Binion, 2016).

Thus, as discussed above, the prior art teaches that both IBD and CDI must be treated. As discussed above, this requires administration of antibiotics to treat the *C. difficile* infection while also administering immunosuppressive compounds such as corticosteroids to treat the inflammation. However, corticosteroids are known to have a negative impact on attempts to treat *C. difficile* infection (Binion, 2016).

In some embodiments of the invention, the polyclonal antibodies are administered to the patient to treat or prevent or prophylactically treat the IBD or the flare of IBD associated with *C. difficile* with the proviso that corticosteroids or other immunosuppressive compounds are not co-administered or subsequently administered to the patient.

Specifically, the polyclonal antibody composition provides a therapeutic and prophylactic treatment for Inflammatory Bowel Disease for example a flare of Inflammatory Bowel Disease associated with *C. difficile*. As discussed in the Examples, the polyclonal antibody composition has been demonstrated to significantly improve the clinical symptoms associated with Inflammatory Bowel Disease, as well as to cure the disease and eradicate *C. difficile* from the patient. That is, as discussed herein, the polyclonal antibody composition comprises polyclonal antibodies raised against *C. difficile* spores which remove the spores from the gastrointestinal tract of the patient, as evidenced by lack of *C. difficile* detection in stool samples from the patients, as discussed below.

As discussed herein, the polyclonal antibody composition was administered to patients by oral administration. Specifically, because the polyclonal antibody composition is formulated with ovalbumin, antibody degradation in the gut by gastric enzymes is significantly reduced, as discussed herein.

Furthermore, the polyclonal antibody composition is derived from human consumable eggs, which are safe for human consumption without any toxicity. The US FDA considers egg-derived products as GRAS (Generally Recognized as Safe). This is evidenced by the successful treatment of over 100 patients without side-effects. It is also important to note that these patients had severe gastrointestinal infections and were still able to tolerate oral administration of the polyclonal antibody composition.

As discussed herein, this is possible because the polyclonal antibody composition comprises antibodies against Toxin A, Toxin B and *C. difficile* spores. Consequently, the composition targets the virulence factors of *C. difficile* and also targets the spores of *C. difficile*. As demonstrated below, the polyclonal antibody composition is capable of effective neutralization of toxins, which damage the intestinal mucosa.

Furthermore, the antigens are prepared from full length Toxin A, Toxin B and *C. difficile* spores. In some embodiments, intact full length Toxin A, Toxin B and spores are used although embodiments in which immunogenic fragments thereof are used as antigens are also contemplated. As will be apparent to one of skill in the art and as discussed herein, the advantage of polyclonal antibody preparations compared to monoclonal antibodies is that the polyclonal antibody preparation comprises poly-specific antibodies which recognize and bind to multiple epitopes on a single target. Accordingly, the use of "full length" antigens is preferred for obvious reasons but is not necessarily an essential feature of the invention.

Furthermore, as shown in the examples, the polyclonal antibody composition comprises antibodies which bind to virulence factors and/or toxins from *C. difficile* clinical isolates with diverse genetic makeup, having different ribotypes and toxinotypes in an antibody dose-dependent manner, as discussed below.

As can be seen in the examples, the oral dosage and treatment regime used varied depending on the patient but was typically 10 or 20 g per day for 10 consecutive days.

In one aspect of the invention, there is provided a method of preparing a polyclonal antibody composition for treating or preventing or prophylactically treating Inflammatory Bowel Disease or a flare of Inflammatory Bowel Disease associated with *C. difficile* comprising:
 a) Immunizing a first group of egg-laying hens with an antigen prepared from *Clostridium difficile* Toxin A;
 b) immunizing a second group of egg-laying hens with an antigen prepared from *Clostridium difficile* Toxin B;
 c) immunizing a third group of egg-laying hens with an antigen prepared from *Clostridium difficile* spores;
 d) collecting eggs laid by said first group, said second group and said third group; and
 e) recovering polyclonal antibodies from said collected eggs.

The antigens may be administered to the hens in combination with an adjuvant. In some embodiments the adjuvant is MONTANIDE-ISA-70™.

In some embodiments, the hens may be inoculated or immunized more than once prior to collection of the eggs.

In some embodiments, the polyclonal antibodies are recovered from the collected eggs by freeze-drying the eggs or by spray-drying the eggs.

Preferably, the polyclonal antibody composition has a reciprocal titer of <128,000.

As will be appreciated by one of skill in the art, each group of hens may comprise 5, 10, 15, 20, 30, 40, 50, 75, 100, 150, 200, 250, 500, 1000, 2000, 3000, 4000, 5000 or more hens.

Furthermore, unlike the difficulties encountered with the production of large quantities of colostrum-based or IVIg antibody products, the inventors have found that 1000 immunized chickens will produce 750 Kg of polyclonal antibody composition in a 2-month time period. As will be apparent to one of skill in the art, this corresponds to the therapeutic treatment of 3750 IBD patients at 10 g dosage daily for 10 days.

As will be appreciated by one of skill in the art, more hens in each group means lower potential variability between batches of the polyclonal antibody composition.

Specifically, each group of immunized hens will produce eggs containing polyclonal antibodies against *Clostridium difficile* Toxin A, Toxin B or spores for several months and as such, because of the number of immunized animals, the consistency of the polyclonal antibody composition will be less variable both within groups of hens immunized with the same antigen and compared to subsequent groups of immunized hens.

As will be appreciated by one of skill in the art, the collected eggs may be pooled prior to recovery of the polyclonal antibodies by freeze drying or spray drying. Alternatively, the polyclonal antibodies from each group may be recovered separately and then combined.

As will be appreciated by one of skill in the art, the Toxin A, Toxin B and spore antigens may be prepared using any suitable means known in the art, for example, using the methods exemplified in the Examples provided below. While in some embodiments, full-length toxins and intact spores are used as part of the antigen, immunogenic fragments of either one or both of the toxins and/or the spores may be used in antigen preparation, as discussed herein.

Thus, in one embodiment, the polyclonal antibody composition of the present invention comprises egg-derived antibodies that bind to and/or neutralize *C. difficile* Toxin A or a fragment thereof, *C. difficile* Toxin B or a fragment thereof, and that bind to *C. difficile* spores and effectively neutralize the spores by preventing and/or interfering with the ability of the spores to bind to the mucosal lining of the gastrointestinal tract of the infected host, as discussed below.

As demonstrated in the examples below, the polyclonal antibodies prepared herein demonstrate effective binding of Toxin A, Toxin B and spores as well as toxin neutralization from a number of different *C. difficile* isolates. As will be apparent to one of skill in the art, this demonstrates the advantage of polyclonal antibodies compared to monoclonal antibodies as the various antibodies within the polyclonal antibody composition will bind to multiple neutralizing epitopes on the toxins and spores.

According to another aspect of the invention, there is provided the use of the polyclonal antibody composition described above to treat or prevent or prophylactically treat Inflammatory Bowel Disease, for example, a flare of Inflammatory Bowel Disease associated with *C. difficile*, as discussed herein.

In one aspect of the invention, there is provided a method for treating or preventing or prophylactically treating Inflammatory Bowel Disease, for example, a flare of Inflammatory Bowel Disease associated with *C. difficile* comprising administering to an individual in need of such treatment an effective amount of a polyclonal antibody composition, said polyclonal antibody composition being prepared by a method comprising:

a) immunizing a first group of egg-laying hens with an antigen prepared from *Clostridium difficile* Toxin A;

b) immunizing a second group of egg-laying hens with an antigen prepared from *Clostridium difficile* Toxin B;

c) immunizing a third group of egg-laying hens with an antigen prepared from *Clostridium difficile* spores;

d) collecting eggs laid by said first group, said second group and said third group;

e) recovering polyclonal antibodies from said collected eggs; and f) administering a therapeutically effective amount of the polyclonal antibodies to an individual in need of such treatment.

In another aspect of the invention, there is provided a polyclonal antibody composition for treating or preventing or prophylactically treating Inflammatory Bowel Disease for example a flare of Inflammatory Bowel Disease associated with *C. difficile* characterized in that said polyclonal antibody composition being prepared by a method comprising:

a) immunizing a first group of egg-laying hens with an antigen prepared from *Clostridium difficile* Toxin A;

b) immunizing a second group of egg-laying hens with an antigen prepared from *Clostridium difficile* Toxin B;

c) immunizing a third group of egg-laying hens with an antigen prepared from *Clostridium difficile* spores;

d) collecting eggs laid by said first group, said second group and said third group; and e) recovering polyclonal antibodies from said collected eggs.

As discussed herein, the effective amount may be for example 2 to 40 g or 2 to 30 g or 2 to 20 g or 5 to 40 g or 5 to 30 g or 5 g to 20 g or 10 to g of the polyclonal antibody composition, as discussed herein.

The polyclonal antibody composition may be administered daily to the individual in need of such treatment until treatment has been concluded, as discussed herein. For example, the polyclonal antibody composition may be administered for a period of at least 7 days, 7-21 days, 7-10 days, 7-14 days, at least 10 days or 10-14 days.

In some embodiments of the invention, a polyclonal antibody preparation referred to herein as IM-01, prepared as described above is provided and used.

The reactivity and specificity of IM-01 was established by evaluating the binding characteristics against *C. difficile* toxin A and *C. difficile* toxin B antigens using an ELISA immunoassay (FIG. 1). The result shows that IM-01 demonstrated strong reactivity (binding) to *C. difficile* Toxin A and B in a dose dependent manner.

Functional activities were evaluated in vitro, using cell-based assays, to determine neutralization ability of IM-01 against Toxin A and Toxin B-mediated cytotoxicity (FIG. 2). The result shows that IM-01 neutralized *C. difficile* Toxin A and Toxin B-mediated cytotoxicity in vitro in a dose dependent manner.

As discussed herein, one aspect of the invention provides a method of neutralizing, inhibiting, blocking, reducing, ameliorating, curing, or treating *C. difficile* infection in a subject suffering from Inflammatory Bowel Disease comprising administering to the subject an effective amount of the above-described polyclonal antibodies in a therapeutically effective amount that is sufficient to neutralize, inhibit, block, reduce, ameliorate, cure, or treat *C. difficile*-associated disease or CDAD, including symptoms such as mild to severe diarrhea and in some cases associated with severe, life threatening complications, such as pseudomembranous colitis, toxic megacolon, bowel perforation, sepsis and death, in the subject.

Furthermore, as discussed above, in some embodiments of the invention, there is provided the proviso that the immunosuppressive compounds such as corticosteroids are not co-administered or administered subsequent to administration of the polyclonal antibodies.

As discussed above and as known in the art, immunosuppressive therapies such as corticosteroids are in fact associated with negative outcomes of *C. difficile* treatments.

As discussed herein, *C. difficile* exists as spores within the animal and returns to vegetative growth once growth conditions are more favorable, that is, once antibiotic therapy has ceased.

However, the polyclonal antibody composition, designated herein as IM-01, in addition to comprising antibodies which bind to and neutralize toxins A and B, also comprises antibodies against *C. difficile* spores. The binding of these antibodies to the spores promotes removal of the spores from the animal's gastrointestinal tract.

Furthermore, because the composition comprises polyclonal antibodies, multiple epitope targets on toxin A and B and the spores are bound by the antibodies of the composition. As a result, variations between strains are not as much of a concern as it can be with monoclonal antibody preparations which recognize only a single epitope.

In addition, the polyclonal antibody material is prepared from the eggs of a large number of immunized animals over a long period of time, thereby reducing concerns regarding the reproducibility and consistency of the polyclonal antibody material.

Finally, the polyclonal antibody material is prepared with a sufficiently high titer that therapeutic treatment of humans is possible, as discussed herein. Specifically, as discussed herein, the polyclonal antibody composition has a reciprocal titer of <128,000.

Thus, in summary, the polyclonal antibody composition of the present invention provides a distinct advantage over other therapies in that it is able to inhibit the biological action of toxins A and B of *C. difficile* and the spores of *C. difficile*. Moreover, the polyclonal antibody material of the present invention can be produced with very high titres. The antibodies of the present invention may also be used prophylactically to prevent the onset of Inflammatory Bowel Disease in a patient known to have or at risk of developing *C. difficile* infection along with Inflammatory Bowel Disease, as discussed herein.

As discussed herein, the *C. difficile* may be an antibiotic resistant and/or hypervirulent strain. For example, the *C. difficile* strain may be CCL678, HMC553, Pitt45, CD196, montreal 5, montreal 7.1, MH5, Pitt2, CCL14137, UVA17, UVA30/TL42, or Pitt7.

The invention also embraces a corresponding method for prevention or treatment of IBD, for example, a flare of IBD associated with *C. difficile*, said method comprising oral administration of the polyclonal antibody composition of the present invention to a patient in need of such treatment. The patient in need of such treatment can be an individual who has been previously diagnosed with an IBD, for example, ulcerative colitis or Crohn's disease. The individual may also have been diagnosed as being infected with *C. difficile*, although the individual may be considered to be an asymptomatic carrier of *C. difficile*. The individual may have one or more symptoms of IBD (for example, mild self-limiting diarrhoea, abdominal pain, fever and loss of appetite or life-threatening conditions such as pseudomembranous colitis and cytotoxic megacolon) or may be an individual who has previously had an initial episode or subsequent flare of IBD and is experiencing symptoms consistent with an IBD flare, particularly an IBD flare associated with *C. difficile*. The present invention provides an effective means for preventing, suppressing, treating or treating prophylactically IBD or a symptom thereof or a flare of IBD associated with *C. difficile*.

In one embodiment, said method of treating or preventing or prophylactically treating IBD or a flare of IBD associated with *C. difficile* comprises oral administration of the polyclonal antibody composition of the present invention to a patient suffering from the symptoms of IBD. This can be accomplished using a therapeutically effective amount of the antibodies. Such administration may be effected by repeated administrations of antibody compositions of the present invention, for a prolonged period of time.

A therapeutically effective amount refers to the amount of the antibodies, which when administered to a patient for treating CDI/IBD, or at least one of the clinical symptoms of IBD, is sufficient to affect such treatment of the disease, or symptom. The therapeutically effective amount can vary depending, for example, on the disease, and/or symptoms of the disease, severity of the disease, and/or symptoms of the disease, the age, weight, and/or health of the patient to be treated, and the judgment of the prescribing physician. An appropriate therapeutically effective amount in any given instance may be ascertained by those skilled in the art or capable of determination by routine experimentation.

In another embodiment, said method of preventing IBD comprises oral administration of the polyclonal antibody composition of the present invention to a patient with IBD flares associated with *C. difficile*. This can be accomplished using a prophylactically effective amount of the antibodies prior to the onset or in the very early stages of IBD. Such administration may be effected by repeated administrations of antibody compositions of the present invention, for a prolonged period of time or at any time when the patient feels as though a flare is imminent or possible.

The dosage ranges for administration of the antibodies of the present invention are those to produce the desired therapeutic effect. It will be appreciated that the dosage range required depends on the precise nature of the composition, the nature of the formulation, the age of the patient, the nature, extent or severity of the patient's condition, contraindications, if any, and the judgement of the attending physician.

As discussed in the examples, daily dosages of 10 g and 20 g of the IM-01 polyclonal antibody powder have been administered to human patients suffering from IBD for a period of 10 days and have successfully treated these human patients. While these dosages have been well tolerated by patients suffering from severe gastrointestinal trauma, other suitable effective amounts may be determined through routine experimentation and optimization. Variations in these dosage levels can be adjusted using standard empirical routines for optimisation as well as in consideration of other factors such as for example the age, general condition and severity of symptoms of the subject, as discussed herein.

As discussed herein, the dosage of 10 g or 20 g per day was selected based on the data from a preclinical animal study wherein *C. difficile* infected piglets were treated. Each piglet (1.8 Kg-2.00 Kg) received 0.6 g of IM-01 per day. Based on an average human body weight of 70 Kg, about 35× that of the pigs, this converts to approximately 20 g. Alternatively, the dosage amount may be calculated as 0.3 g per Kg of the subject or individual or patient. However, as discussed above, other amounts may be administered, depending on multiple factors, including but by no means limited to the age, weight, general condition and severity of symptoms of the individual.

Furthermore, the dosage period may be varied and the 10 days provided above should be viewed as a guideline and not as mandatory. For example, the polyclonal antibody composition may be administered daily at an effective amount of 5 g to 20 g to an individual in need of such treatment for a period of at least 7 days, 7-21 days, 7-14 days, 7-10 days, at least 10 days or 10-14 days.

As will be appreciated by one of skill in the art, the attending physician can determine how long administration of the polyclonal antibody composition should be continued, for example, until the severity of symptoms of IBD has been reduced.

IM-01 may be administered directly to the patient as a powder or the powder may be dissolved in a suitable liquid vehicle, for example, milk or soya milk. As will be appreciated by one of skill in the art, other suitable delivery systems are well known in the art and are within the scope of the invention.

It is also within the scope of the invention to use the antibodies of the invention in oral therapeutic methods for the prevention or treatment of IBD in combination with one another, or as an adjunct to, or in conjunction with, other established therapies normally used in the treatment in IBD. However, as discussed herein and in the examples, it is believed that such additional treatment is likely to be unnecessary.

In other embodiments, an antacid component may be added. In use, said antacid component helps protect the antibodies from the highly acid gastric environment that exists within a patient.

An antacid is any substance, generally a base or basic salt, which counteracts stomach acidity. In other words, antacids are stomach acid neutralizers that raise the stomach pH, ideally above pH 4.0, for a limited time period Antacids perform a neutralization reaction, i.e. they buffer gastric acid, raising the pH to reduce acidity in the stomach.

Examples of suitable antacids for use in the present invention include, but are by no means limited to: Prevacid, Prilosec, gastric-acid suppressant, aluminium hydroxide (eg. Amphojel, AlternaGEL); magnesium hydroxide (e.g. Phillips' Milk of Magnesia); aluminum hydroxide with magnesium hydroxide (e.g. Maalox, Mylanta, Diovol); Aluminum carbonate gel (eg. Basaljel); calcium carbonate (eg. Alcalak, TUMS, Quick-Eze, Rennie, Titralac, Rolaids); sodium bicarbonate (eg. bicarbonate of soda, Alka-Seltzer); magnesium carbonate; magnesium trisilicate; hydrotalcite (eg. $Mg_6Al_2(CO_3)(OH)_{16}.4(H_2O)$; Talcid); bismuth subsalicylate (e.g. Pepto-Bismol); alginates (e.g. sodium alginate, alginic acid); magaldrate with simethicone (eg. Pepsil); any of the above in combination with simethicone for example Asilone, which has three active ingredients, aluminium hydroxide and magnesium oxide neutralise the acid removing the cause of the pain, and dimethicone.

The invention will now be further elucidated by way of examples; however, the invention is not necessarily limited by the examples.

EXAMPLE 1

Manufacturing of Egg-Derived Polyclonal Antibodies, IM-01;

IM-01 is an oral polyclonal antibody therapy for the treatment of *Clostridium difficile* Infection (CDI). IM-01 is produced in chicken eggs following the immunization of laying hens with specific *C. difficile* virulent factor antigens: *C. difficile* toxin A and toxin B, and *C. difficile* spores.
Preparation of Immunogens A *Clostridium difficile* strain isolated from the stool sample of a *C. difficile* infected patient was grown in Brain Heart Infusion (BHI) medium for 16-18 hrs at 37° C. in an anaerobic chamber. The bacteria were harvested by centrifugation to collect the bacterial pellet. For production of spore antigen, *C. difficile* was grown in BHI medium for 16-18 hrs at 37° C. in an anaerobic chamber, followed by spreading the culture on Columbia blood agar plates. The plates were then incubated for 5-7 days, at 37° C. in the anaerobic chamber. The spores were harvested in RO water, washed in RO water, centrifuged at 1400 RPM for 10 minutes, re-suspended in RO water and stored in a freezer.

For preparation of immunogen, 1% formaldehyde was added to the spore suspension and incubated at 37° C. for 24 hours and then dialysed in PBS at 4° C. overnight.

For production of *Clostridium difficile* toxins, *C. difficile* was grown in BHI medium for 5 days at 37° C. in the anaerobic chamber. The purification of the toxin A and toxin B antigens was performed as described by Fu et al 2004, World J. Gastroenterol 10: 2756-2758. The culture supernatant was removed by centrifugation at 800 g for 20 minutes and the toxin containing proteins in the supernatant were then subjected to ammonium sulfate precipitation, by adding 60% of ammonium sulfate. Following incubation at 4° C. overnight, the precipitate was dissolved in 20 mM Tris-HCl buffer pH 7.5 and dialysed against 10 mM acetate buffer pH 5.5 at 4° C. overnight. After dialysis, the precipitate containing toxin A and B was separated by centrifugation and dissolved in 4 mL of 50 nM Tris-HCl buffer. Finally, Toxin A and toxin B were purified by anion-exchange column chromatography using DEAE-Toyoperl and the protein peak containing toxins were eluted with a gradient of 200-400 mM of NaCl 50 nM of Tris-HCl. The purified toxins were concentrated and stored in a freezer until use.

For preparation of immunogens, toxin A and toxin B were fixed with 0.4% of formaldehyde by incubation at 37° C. for 24 hours. Subsequently, the fixed-toxins were then dialysed against PBS at 4° C. overnight.

Immunization of Laying Hens for Production of IM-01 Polyclonal Antibody-Containing Eggs The preparation of the *C. difficile* vaccine, (antigen+ MONTANIDE-ISA-70™ adjuvant), was carried out for the immunization of the hens. The *C. difficile* antigen+adjuvant were prepared by the mixing of the *C. difficile* antigen and the adjuvant at a ratio of 30:70 respectively. The mixture was homogenized to make a uniform suspension prior to the vaccination of the hens.

Pathogen-free, healthy white Bovins hens, 24-25 week-old, were vaccinated with a 0.5 mL of *C. difficile* antigen-adjuvant, with 0.25 mL injected intramuscularly into each side of the pectoral muscles. The vaccination was repeated three times with 3-week intervals between each injection for a total of three vaccinations.
Production of IM-01-Egg-Derived Polyclonal Antibodies Antibody eggs were collected for the first time 3 weeks post-vaccination. These eggs were washed with 0.5% Sodium hypochlorite, broken and the freeze-dried or spray-dried to produce IM-01 polyclonal antibodies. The levels of *C. difficile* polyclonal antibodies in these in-process egg samples were tested by ELISA to determine the reactivity against *C. difficile* antigen(s).

Purity and safety are tested for each batch with the same microbiological techniques used for eggs intended for human consumption. This includes *Salmonella* spp., Coliform and standard plate count as required by Health Canada and CFIA.
Description and Composition of the Polyclonal Antibody Composition IM-01 is a powder for oral suspension. IM-01 is composed of ovalbumin (egg white) and egg yolk. No other excipients are added.

EXAMPLE 2

Specificity and Reactivity of Polyclonal Antibodies IM-01 to *Clostridium difficile* Toxins Using ELISA Assays Shown in FIG. 1

Specificity and reactivity of IM-01 to *C. difficile* toxin A and toxin B antigens was demonstrated using 96-well polyvinyl chloride (PVC) flat bottom ELISA plates coated with 0.2 μg of purified toxin A or toxin B in 100 μL of carbonate-bicarbonate coating buffer each well. The toxin-coated plates were incubated at 4° C. for 16-18 hrs and washed with washing buffer (PBS+0.5% Tween 80). Non-specific sites were blocked after incubation with the blocking buffer (1% skim milk in PBS), the wells were washed with washing buffer and incubated at 37° C. for 2 hours with 100 μL per well of the diluted IM-01 polyclonal antibodies in egg powder or control egg powder derived from the non-immunized chicken eggs. Samples were diluted to determine antibody titers in each of the test and control samples. Subsequently, the antigen-antibody interaction was detected after incubation with alkaline phosphatase-conjugated rabbit anti-chicken IgG at 37° C. for 2 hours, followed by incubation with the alkaline-phosphatase substrate. The reactivity was determined by measuring the absorbance at 405 nm.

As illustrated in FIG. 1, control egg demonstrated very weak reactivity against *C. difficile* toxin A and toxin B antigens with a reciprocal antibody titer ≤16,000. In contrast, the IM-01 polyclonal antibodies showed very strong reactivity against *C. difficile* toxin A and toxin B with a reciprocal antibody titer <128,000, demonstrating that IM-01 egg-derived polyclonal antibodies specifically binds to the *C. difficile* toxin antigens.
Spectrum of Reactivity of Polyclonal Antibodies IM-01 to Toxins Produced by Genetically Diverse *C. difficile* Strains Shown in Table 1

*Clostridium difficile* is a widely distributed pathogen with multiple strain types as determined by PCR ribotyping. Ribotype 027 isolates were found to be the most common strains identified and distributed throughout the North America and some countries in Europe. Other *C. difficile* ribotypes also have been detected from disease patients from North America, Europe, Asia and Australia (Cheknis, A. K. et al. 2009, *Anaerobe* 15(6):230-3).

A strain type classified as NAP/B1/027 was found to be responsible for more than half of the *C. difficile* infected cases with high morbidity and mortality in North America and Europe (Merrigan, M. et al. 2010, *J Bacteriol.* 192(19): 4904-11).

*C. difficile* isolates of NAP/B1/027 have been implicated as hypervirulent strains and linked with disease severity as well as hospital outbreaks worldwide. It has been suggested that these hypervirulent strains produce larger amount of toxins relative to the non-hypervirulent strains, since production of toxins correlated well with the presence and the type of toxin genes. Although the majority of ribotypes with variant strains produced both toxins, many strains produce only TcdB (A– B+) (Rupnik, M. et al., 2001, *Microbiology* 147(Pt 2):439-47; Rupnik, M. 2008, *FEMS Microbiol Rev.* 32(3):541-55). Aside from the two toxin genes (tcdA and TcdB), there are three other genes within the PacLoc: tcdC, tcdR and tcdE (Braun, V et al 1996, *Gene* 181(1-2):29-38). tcdC, which encodes a negative regulator of toxin expression, is highly variable. There are four types of deletions present in different toxinotypes The reactivity of IM-01 polyclonal antibodies was assessed against toxins produced in vitro in the culture supernatant by genetically diverse *C. difficile* strains isolated from patients with *C. difficile* infections. A fixed number of spores from various clinical isolates of *C. difficile* strains were grown in Brain Heart Infusion (BHI) medium for 72 hours. The culture supernatant was separated from the bacterial mass by centrifugation of the broth at 4,000 RPM for 20 minutes.

The ELISA plates were coated with culture supernatant containing *C. difficile* toxins from diverse *C. difficile* strains. The toxin-coated ELISA plates were treated in a similar fashion, as described above. Antibody reactivity with toxins was determined after incubation with 1:2000 dilution of control egg powder obtained from non-vaccinated chickens or IM-01 antibodies. Finally, the toxin-antibody reaction was detected following incubation with alkaline phosphatase-conjugated rabbit anti-chicken IgG at 37° C. for 2 hours, followed by incubation with the alkaline-phosphatase substrate. The reactivity was determined by measuring the absorbance at 405 nm.

c. Toxin-Dose Dependent Binding of Polyclonal Antibodies, IM-01 to Toxins Produced in Culture Supernatant of Diverse *C. difficile* Strains.

Although hypervirulent strains such as NAP/B1/027 have been implicated to produce larger amount of toxins relative to the non-hypervirulent strains, it has also been reported that the amounts were not significantly different from that of non-hypervirulent strains (Merrigan, M. et al 2010).

Consequently, the reactivity of IM-01 polyclonal antibodies was tested against *C. difficile* toxins present in the diluted culture supernatants produced by genetically diverse *C. difficile* strains, with four different ribotypes: 002, 003, 019 and 027. ELISA plates were coated with 10, 100 and 500 times diluted culture supernatants obtained from seven different *C. difficile* strains. The toxin-coated ELISA plates were treated in a similar fashion as described above. Antibody reactivity with toxins was determined after incubation with 1:2000 dilution of control egg powder obtained from non-vaccinated chickens or IM-01 antibodies. Finally, the toxin-antibody reaction was detected following incubation with alkaline phosphatase-conjugated rabbit anti-chicken IgG at 37° C. for 2 hours, followed by incubation with the alkaline-phosphatase substrate. The reactivity was determined by measuring the absorbance at 405 nm and the result is shown in Table 1. The results demonstrate that IM-01 polyclonal antibodies showed strong reactivity (OD value at 405 nm 0.92-1.8) to toxins generated in culture supernatant from genetically diverse *C. difficile* strain with ribotypes: 004, 002, 019, 003, NAP/B2/027 and toxinotypes: 21, 0, 6, 9, 8, 3 and 2.

Figure 2:
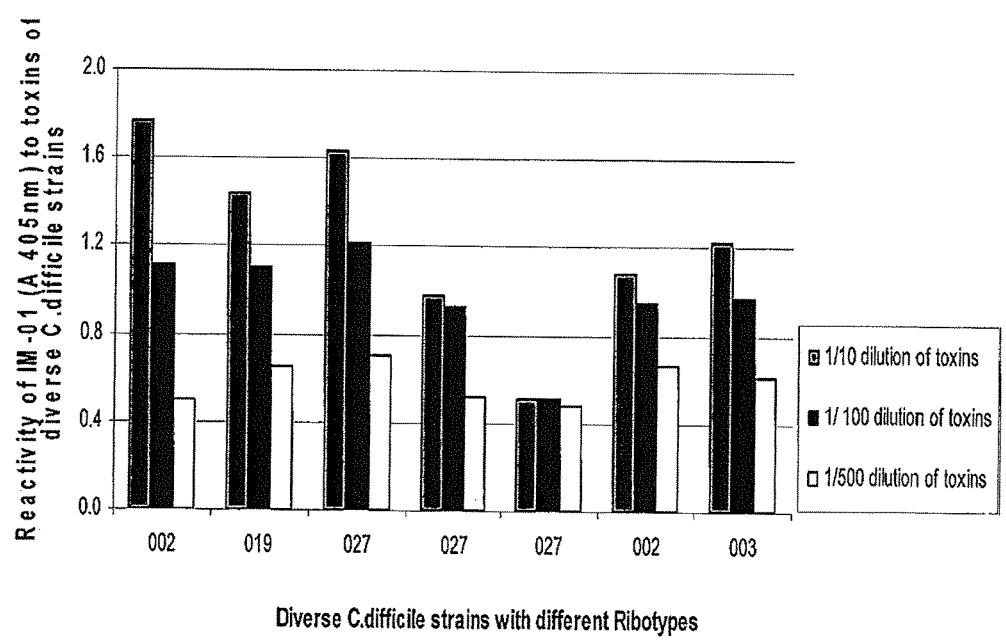

Additional results are shown in FIG. 2. IM-01 polyclonal antibodies showed strong reactivity against toxins produced by all seven clinical isolates of *C. difficile* of four different ribotypes, 002, 003, 019 and 027. However, the reactivity was strongest with the 1/10 dilution and weakest with the 1/500 dilution of culture supernatant.

It was concluded that clinical isolates of *C. difficile* produced variable amounts of toxins in vitro in the culture supernatants and IM-01 antibodies exhibited strong reactivity, but the reactivity was determined to be toxin-concentration dependent. Binding reactivity of IM-01 polyclonal antibodies to spores produced by genetically diverse *C. difficile* strains as shown in Table 2

Although the toxins are responsible for symptoms of the disease, endospore formation is also an important factor that contributes to the disease transmission and recurrence of disease. Spores can survive, germinate, and proliferate in the gut following exposure to antibiotic treatment (Carlson, P. E. et al. 2013, *Anaerobe* 24:109-16). Since *C. difficile* strains exhibited considerable inter-strain heterogeneity, various toxigenic clinical isolates were selected with genetic diversity, based on ribotype and toxinotype, in order to determine reactivity of IM-01 antibodies to the spores produced by these diverse *C. difficile* strains.

ELISA plates were coated with 0.4 µg/mL of spore antigen and incubated overnight at 4° C. The plates were washed as described above. To determine antibody reactivity to spores, spore antigen-coated ELISA plates were incubated with either control egg powder from non-vaccinated chickens or IM-01 antibodies at 1:4000 dilutions, followed by incubation with alkaline phosphatase-conjugated rabbit anti-chicken IgG. Subsequently, the antigen-antibody interaction was detected after incubation with the substrate. The reactivity was determined by measuring the absorbance at 405 nm.

It was demonstrated that the control egg powder showed weak reactivity ($A_{405}$<0.3) against *C. difficile* spores. In contrast, IM-01 antibodies showed strong reactivity ($A_{405}$ 0.87-2.25) against *C. difficile* spores of genetically diverse origin, specifically, 10 different strains and 5 different ribotypes. The results are shown in Table 2.

It was concluded that IM-01 antibodies can bind to spores generated by genetically diverse *C. difficile* strains.
Binding of IM-01 Polyclonal Antibodies to *C. difficile* Bacteria of Genetically Diverse Origin Shown in Table 3

To determine the binding pattern of IM-01 to *C. difficile* bacteria with genetically diverse origins, ELISA plates were coated with formalin-fixed *C. difficile* bacteria, 0.3 µg/100 µL/well, following the method described above. The ELISA plates were incubated 16-18 hours at 4° C., then washed and further incubated with a fixed concentration at 1:4,000 dilutions of IMM-001 antibodies. Subsequently, the plates were washed and further incubated with alkaline phosphatase-conjugated rabbit anti-chicken IgG. The antigen-antibody interaction was detected after incubation of the plates with the substrate and absorbance at 405 nm was measured. The results are shown in Table 3.

It was concluded that IM-01 antibodies exhibited strong reactivity ($A_{405}$ 0.92-1.8) to *C. difficile* of diverse origin, when the control showed very weak reactivity ($A_{405}$<0.38).

The overall conclusion is that egg-derived polyclonal antibodies IM-01 demonstrated strong reactivity to *C. difficile* virulent antigens of genetically diverse clinical isolates of *C. difficile* strains.

EXAMPLE 3

Figure 3:
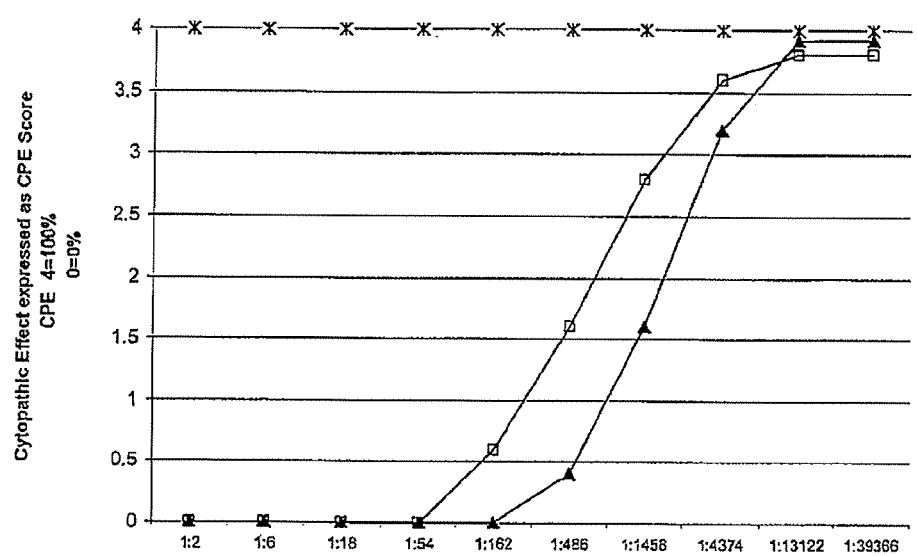

Assessment of Efficacy of IM-01 Polyclonal Antibodies In Vitro in Toxin Neutralization Ability of IM-01 Antibodies Using IMR-90 Cell Assay Shown in FIGS. 3, 4 & 5

The cellular cytotoxicity assays were designed to determine the functional activity and mode of action of IM-01 antibodies, since the IM-01 antibodies recognized *C. difficile* toxin antigens in binding studies discussed above.

The human lung fibroblast cell line, IMR-90, cell-based in vitro assay was used to determine *C. difficile* toxin neutralizing ability of IM-01, since IMR-90 cells are sensitive to both toxin A and toxin B. Briefly, IMR-90 cells ($1 \times 10^5$/well) were incubated with *C. difficile* toxin A&B alone or toxin A&B+IMM-001 antibodies for 24 hours at 37° C. The cytopathic effects were determined by observing the percentage of cells that had become rounded in the presence of the toxins. When there is no cytopathic effect, i.e. cells that had not become rounded with toxin in presence of antibodies, toxin was considered 100% neutralized.

As shown the results in FIGS. 3, 4 and 5, no toxin neutralization activity was detected when the cells were incubated with toxin alone. In contrast, maximum neutralization activity (100%) was achieved when the toxin was mixed with IMM-001 antibody concentration at 6.17 µg/mL or higher. However, the toxin neutralization ability diminished to zero when the lowest amount of IM-01 antibody (0.06 µg/mL) was added to the toxin.

It has been concluded that IM-01 egg-derived polyclonal antibodies are capable of neutralizing the cytopathic effects mediated by *C. difficile* toxin A and toxin B on IMR-90 cells in vitro and the efficacy of toxin neutralization is IM-01 antibody concentration-dependent.

EXAMPLE 4

Spectrum of Toxin Neutralizing Potency of IM-01 with Toxins Produced by Genetically Diverse *C. difficile* Strains in IMR-90 Cell Line Based Assay Shown in Table 4

Since *C. difficile* exhibited considerable inter-strain heterogeneity in the genes encoding toxin A and B, these studies were undertaken to determine the toxin neutralization ability of IM-01. A panel of genetically diverse *C. difficile* strains comprised of seven toxigenic clinical isolates with four different ribotypes was selected to assess ability of IM-01 antibodies to neutralize toxins produced by these strains.

The cell-based assay was same as described above, except the toxin source. The culture supernatant from various *C. difficile* strains were used as toxin sources in this study, instead of the purified toxin from VPI 10463 that was used in the previous example. The IMR-90 cell-based assay was performed to determine the antibody concentration needed for 100% neutralization of toxins produced by these diverse strains.

It was concluded from the results that the antibody concentration needed to neutralize 100% toxin neutralization varied with the toxins produced in culture supernatant by diverse *C. difficile* strains. The highest amount 300 µg/mL and lowest amount 0.7 µg/mL of IM-01 antibodies is needed to neutralize 100% cytopathic activity mediated by toxins produced by genetically diverse *C. difficile* strains, as shown in Table 4.

Efficacy of IM-01 in Neutralizing Toxins from *C. difficile* Hypervirulent NAP/B1/027 Strain Using T-84 Cell Line Based Assay, Shown in FIG. 6

As the IMR-90 cell line is considered to be sensitive to *C. difficile* toxins A and B, the human colonic tumor cell line, T-84, is considered to be more sensitive to *C. difficile* toxin A. A study was designed to confirm the efficacy of IM-01 antibodies at neutralizing toxins produced by hypervirulent *C. difficile* strain NAP/B1/027, using a cell-based assay with T-84 cells.

The T-84 cells were incubated with either *C. difficile* toxins A and B alone or in combination (toxin A & B+polyclonal antibodies) for 24 hours at 37° C. The cytopathic effects were determined by observing the percentage of cells that had become rounded.

It was concluded from the results in FIG. 6, that toxin A and B individually demonstrated 100% cytopathic effect with no toxin neutralization on T-84 cells. *C. difficile* toxin+ control IgY in normal egg showed 85-90% cytopathic effect with 10-15% toxin neutralization on T-84 cells. In contrast, following incubation with toxin A & B+IM-01 antibodies demonstrated 0% cytopathic effect with 100% toxin neutralization. Furthermore, the toxin neutralization ability of IM-01 antibodies is determined to be antibody dose-dependent.

EXAMPLE 5

Assessment of In Vitro Growth Inhibition Activity of IM-01 Polyclonal Antibodies a. As *C. difficile* spores play a key role in the colonization, transmission and pathogenesis of CDI, experiments were designed to determine efficacy of IM-01 antibodies in vitro. *C. difficile* spores from 3 different isolates of hypervirulent *C. difficile* strain NAP/B1/027 were incubated with control IgY from eggs from non-immunized chickens or IM-01 antibodies for 24 hours to determine antibody effect on growth of *C. difficile*.

As shown in FIG. 7, that the 90-260 colonies were detected after incubation of a fixed number of *C. difficile* spores with control material, and the spore multiplication rate was determined to be different among the three hypervirulent strains. In contrast, only 5-20 colonies were detected following incubation of the same number of spores of the three genetically different *C. difficile* hypervirulent strains with IM-01 antibodies.

Based on the results shown in FIG. 8, it was concluded that IM-01 antibodies inhibited >80% growth of all the three *C. difficile* isolates of NAP/B1/027.

EXAMPLE 6

Assessment of IM-01 Antibodies on Inhibition of Adhesion of *C. difficile* to Caco-2 Cells as Shown in Table 5.

Although the role of toxin A and toxin B in pathogenesis of *C. difficile* infection is established, the exact sequence of pathological events leading to disease is not well understood, particularly on adhesion on human intestinal mucosa.

We studied the effect of IM-01 polyclonal antibodies on adhesion of *C. difficile* bacteria to epithelial cells in vitro by using human colonic epithelial cell line Caco-2. This cell-line closely resembles small intestinal epithelial cells and has been used to study mechanisms of adherence and invasion of many pathogenic bacteria.

To quantify the effect of IM-01 polyclonal antibodies on inhibition of C. difficile attachment to Caco-2 cell, cells were cultured and maintained using the ATCC protocol. Caco-2 cells were grown in cover slips in 24-well plate for 48 hours. Then medium from each well was removed, and Caco-2 cells were incubated with 100 μL of C. difficile bacteria of NAP/B1/027 ($10^7$ cfu/mL) in presence of 100 μL control material or IM-01 antibodies at 1 mg/ml, 0.5 mg/ml or 0.25 mg/mL for 2 hours at 37° C. Following incubation, Caco-2 cells were then rinsed with PBS to remove non-adherent bacteria. Cell-associated bacteria were fixed with methanol and stained with Giemsa. Once the cover slips were dried, the number of adherent C. difficile bacteria was enumerated per field under microscope and the numbers were counted in 26 fields for each cover slip.

As shown in the results, in Table 5, the average number of C. difficile bacteria detected in each field following incubation with control egg powder (IgY) ranged from 29.7-54.1. In contrast, the number of C. difficile bacteria detected after incubation with IM-01 polyclonal antibodies was much lower, ranging from 13.9-16.1 per field. The highest inhibition of C. difficile adhesion to Caco-2 cells (73%) was achieved after incubation with IM-01 antibodies at 0.25 mg/mL.

Based on the results shown in Table 5, it was concluded that IM-01 antibodies inhibited 73% adhesion of hypervirulent C. difficile isolate of NAP/B1/027 strain onto Caco-2 cells.

EXAMPLE 7

Formulation of IM-01 Polyclonal Antibodies and Assessment of Gut Stability for Oral Administration as Shown in FIG. 9.

The limitations of oral administration of antibodies are mainly due to degradation by proteolytic enzymes, such as Trypsin and Cymotrypsin, present in the gut. The proteolytic enzymes present in digestive secretions block large molecules, such as antibodies, from reaching the gut and the colon, where IM-01 is required to interact with C. difficile toxins and spores. The proteolytic enzymes in digestive secretions are one of the factors that inhibit optimal amounts of antibody from reaching the gut.

It has been demonstrated in several studies that ovalbumin present in chicken egg white is a potent inhibitor of the proteolytic activity of trypsin/chymotrypsin and can protect the antibody molecules from the digestive enzymes in gut.

IM-01 is produced and formulated with egg white that includes ovalbumin for protection from the enzymatic digestion in gut. In order to confirm the gut stability of IM-01, experiments were designed to determine gastric stability of IM-01 in vitro.

Formulations were assessed for gastric stability by exposure to simulated gastric conditions. Simulated gastric and intestinal conditions were prepared using a protocol described in USP, Pharmacopeial Convention Council of Express (2004) 27, volume 22 p 2728. Antibody formulation IM-01 was mixed with a solution of 3.2 mg/ml pepsin in 30 mm NaCl at pH 1.2, in the ratio of 1 part pepsin solution to 250 parts of antibody solution and incubated for 360 minutes at 37° C. Similarly, IM-01 antibody was mixed with solution of 10 mg/ml pancreatin in 50 mM potassium phosphate buffer at pH 6.8, in the ratio of 1 part of pancreatin solution to 50 parts antibody solution and incubated for 360 minutes 37° C.

Subsequently, antibody-mediated toxin neutralization activity was measured before and after enzymatic treatment of IM-01 antibodies in the IMR-90 cell based assay as described elsewhere herein, to assess functional integrity of the polyclonal antibodies of IM-01.

As shown in FIG. 9, the toxin neutralization ability of IM-01 antibodies was not altered even after treatment with pepsin and pancreatin.

It was concluded that, since toxin-neutralization ability had not been altered by proteolytic enzymes, IM-01 in its current formulation is protected from digestive enzymes under simulated gastric and intestinal conditions.

EXAMPLE 8

Antibody Dose Selection for Treatment of Patients with C. difficile Infections, Efficacy of IM-01, C. difficile Egg Derived Polyclonal Antibodies in Pigs Clostridium difficile is a ubiquitous bacterium in the environment that has been recognized as an important emerging pathogen in both humans and animals. Veterinary medicine has highlighted the role of animals as reservoirs for C. difficile. In recent years, C. difficile has been identified as causing neonatal diarrhea in pigs (Songer, J. G. and Uzal, F. A. 2005; Squire, M. M. et al 2013).

A proof-of-concept study was planned in animals to determine efficacy of IM-01 in the prevention and treatment of C. difficile-induced diarrhea in piglets, since 3-7 day old piglets are highly susceptible to C. difficile diarrhea and C. difficile enteritis.

C. difficile infected piglets (15) on a farm in Minnesota, Minn., were used to measure the efficacy of IM-01 against C. difficile enteritis. The C. difficile infection was confirmed by C. difficile toxin positive stool results from Veterinary Diagnostic Laboratory. Subsequently, C. difficile infected piglets were fed 0.6 g of IM-01 once a day for 2 days. It was verbally reported by the farm manager that all of the infected piglets had recovered from the C. difficile-enteritis.

Two other experiments were performed on different pig farms in Canada, using the same protocol, to treat C. difficile enteritis. Two veterinarians were on site to help. Subsequently, both veterinarians verbally reported that all infected piglets (5 in each farm) had recovered from C. difficile Enteritis following oral administration of IM-01 antibodies.

EXAMPLE 9

Treatment of Patients with C. difficile Infections and IBD (UC & CD) with IM-01 Therapy—10 g or 20 g/Day×10 Consecutive Days at the Center for Digestive Diseases, Sydney, Australia 1. A 33-year old female patient diagnosed previously with ulcerative colitis (UC) was suffering from diarrhea with soft porridge stool 5 times per day, urgency, and gas. Her stool sample was tested positive for C. difficile in culture. Previously, she received treatment with salazopyrine 3bd and ciproxin 250 mg bd. She was given with 10 g of IM-01 polyclonal antibody powder orally per day for 10 consecutive days. The patient was cured with no clinical symptoms. Her post-antibody treatment stool samples at 3-week and 12-week tested negative for C. difficile in culture. As she showed marked improvement, her all medications for treatment of UC were stopped.

2. A 49-year old female patient, who had a history of Crohn's disease (CD) since 2006, had symptoms of rectal bleeding, diarrhea, with sub-umbilical pain, but no hemorrhoids in the past 6 weeks. Her stool sample tested positive for C. difficile toxins by EIA. Previously, she received treatment with maxalon, nexium, imuran, effexor, capinol, ciproxin and vancomycin. She was given with 20 g of IM-01 polyclonal antibody powder orally per day for 10 consecutive days. The patient was cured with significant improvement in clinical symptoms and her post-antibody treatment stool sample was tested negative for *C. difficile* toxins by EIA.

3. A 42-year old female patient was suffering from Crohn's disease (CD), abdominal pain, semi-formed stools 2 per day and joint pain. Her stool sample tested positive for *C. difficile* toxin. She was given with 20 g of IM-01 polyclonal antibody powder orally per day for 10 consecutive days. The patient was cured with marked improvement in clinical symptoms, decreased joint pain, no abdominal pain, stool 1/day. Her post antibody-treatment stool sample was tested negative for *C. difficile* in culture.

4. A 35 year old male patient with a history of Ulcerative colitis (UC) had clinical symptoms of blood on wiping, no mucus. He was not given any prior treatment. His stool sample tested positive for *C. difficile* in culture. He was given with 20 g of IM-01 polyclonal antibody powder orally per day for 10 consecutive days. The patient was cured with marked improvement in clinical symptoms, His post-antibody treatment stool sample was tested negative for *C. difficile* in culture.

5. A 49 year-old male patient had Ulcerative colitis and rectal bleeding. There was no information regarding his previous treatment. His stool sample was positive for *C. difficile* in culture; so he was treated with oral antibody therapy with IM-01. He was given with 20 g of IM-01 polyclonal antibody powder orally per day for 10 consecutive days. The patient was cured with marked improvement in clinical symptoms, His post-antibody treatment stool sample tested negative for *C. difficile* in culture.

6. A 31 year-old female patient suffered from Ulcerative colitis (UC), rectal bleeding and urgency. Her stool sample tested positive for *C. difficile* in culture. Previously, she was treated with salofalk 1 g/day and ciprofloxacin 250 mg. She was given with 10 g of IM-01 polyclonal antibody powder orally per day for 10 consecutive days. The patient showed with marked improvement in clinical symptoms with semi-formed stools, decrease urgency, no blood and mucus in stools. Her post-treatment stool sample tested negative for *C. difficile* in culture.

7. A 60-year old female patient suffered from Crohn's disease (CD) with epigastric pain. Her stool sample tested positive for *C. difficile* in culture. Previously, she received treatment with Anti-MAP, metronidazole, and ciprofloxacin. She was given with 20 g of IM-01 polyclonal antibody powder orally per day for 10 consecutive days. The patient showed with marked improvement in clinical symptoms. Her post-antibody treatment stool sample was tested negative for *C. difficile* in culture.

The scope of the claims should not be limited by the preferred embodiments set forth in the examples but should be given the broadest interpretation consistent with the description as a whole.

TABLE: 1

Reactivity of IM-01 polyclonal antibodies to *C. difficile* toxins produced by genetically diverse *C. difficile* strains

| Diverse *C. difficile* strains | Ribotypes | Toxinotypes | TcdC | Binary Toxin | Control IgY Reactivity with *C. difficile* Toxins by ELISA ($OD_{405}$) | IM-01 reactivity with *C. difficile* Toxins by ELISA (A405 nm) |
|---|---|---|---|---|---|---|
| 2-14 | 004 | 21 | wt | positive | 0.3 | 1.56 |
| 3-31 | 002 | 0 | wt | negative | 0.15 | 1.40 |
| 3-32 | 002 | 6 | 30 bp | positive | 0.25 | 1.32 |
| 3-39 | 019 | 9 | wt | positive | 0.29 | 1.29 |
| 4-12 | 003 | 8 | wt | negative | 0.28 | 1.27 |
| 5-31 | NAP/B1/027 | 3 | del | positive | 0.38 | 1.47 |
| 6-15 | 002 | 2 | wt | negative | 0.31 | 1.40 |
| 6-30 | NAP/B1/027 | 3 | del | positive | 0.37 | 1.20 |
| 10-7 | NAP/B1/027 | 3 | del | positive | 0.34 | 0.92 |
| 92146 | 002 | 0 | wt | negative | 0.29 | 1.1 |
| VPI-10463 | 003 | 0 | wt | negative | 0.31 | 1.8 |

TABLE 2

Reactivity of IM-01 polyclonal antibodies to *C. difficile* spores produced by genetically diverse *C. difficile* strains

| Diverse *C. difficile* strains | Ribotypes | Toxino-types | Control IgY Reactivity with *C. difficile* spores by ELISA (A405 nm) | IM-01 reactivity with *C. difficile* spores by ELISA (A405 nm) |
|---|---|---|---|---|
| 2-14 | 004 | 21 | 0.31 | 1.25 |
| 3-31 | 002 | 0 | 0.18 | 1.42 |
| 3-32 | 002 | 6 | 0.20 | 0.78 |
| 3-39 | 019 | 9 | 0.30 | 1.15 |
| 4-12 | 003 | 8 | 0.31 | 1.20 |
| 5-31 | NAP/B1/027 | 3 | 0.35 | 0.87 |
| 6-15 | 002 | 2 | 0.31 | 1.04 |
| 6-30 | NAP/B1/027 | 3 | 0.33 | 0.98 |
| 10-7 | NAP/B1/027 | 3 | 0.34 | 2.23 |
| 92146 | 002 | 0 | 0.28 | 1.22 |

TABLE 3

Reactivity of IM-01 polyclonal antibodies to *C. difficile* bacteria of diverse genetic origin

| Diverse *C. difficile* strains | Toxino-types | Ribotypes | IM-01 Reactivity with *C. difficile* by ELISA (A 405 nm) |
|---|---|---|---|
| 5-31 | 3 | NAP1/B1/027 | 0.92 |
| 6-30 | 3 | NAP1/B1/027 | 0.95 |
| 10-7 | 3 | NAP1/B1/027 | 0.88 |
| 92146 | 0 | 002 | 0.80 |
| VPI 10463 | 0 | 003 | 0.72 |

TABLE 4

Toxin Neutralization ability of IM-01 antibodies to toxins
produced by genetically diverse C. difficile strains

| Diverse C. difficile strains tested | Ribotypes | Toxino-types | 100% Neutralizing Efficacy of IM-01 (antibody concentration µg/mL) to toxins generated from C. difficile strains with diverse Ribotypes |
|---|---|---|---|
| 3-32 | 002 | 6 | 100 |
| 3-39 | 019 | 9 | 50 |
| 5-31 | NAP/B1/027 | 3 | 300 |
| 6-30 | NAP/B1/027 | 3 | 0.7 |
| 10-7 | NAP/B1/027 | 3 | 60 |
| 92146 | 002 | 0 | 60 |
| VPI 10463 | 003 | 0 | 20 |

TABLE 5

Effect of IM-01 polyclonal antibodies on inhibition
of C. difficile adhesion onto Caco-2 cells

| Incubation at concentration(s) | Average number of adherent C. difficile bacteria detected per microscopic field | | Percent adherence inhibition compared with control IgY |
|---|---|---|---|
| | Control IgY | IM-01 antibodies | |
| 1.0 mg/mL | 29.7 | 14.9 | 42% |
| 0.5 mg/mL | 42.1 | 16.1 | 55% |
| 0.25 mg/ml | 54.1 | 13.9 | 73% |

REFERENCES

1. Paresdes-Sabja, D and Sarker, M. R. J Med. Microbial. 61: 1208, 2012
2. IMS Health incorporated information service: CDM Hospital database for full year 2012.
3. US Department of Health & Human Services. Agency for Health Care Research and Quality, Jan. 25, 2012.
4. Miller B. A. et al. Infect Control Hosp Epidemiol. 32:387, 2011.
5. (APIC) National Prevalence study for *Clostridium difficile* in US Healthcare Facilities. Nov. 11, 2008.
6. Agency for healthcare research and Quality. Statistical Brief #124. *Clostridium difficile* infections (CDI) in hospital stays, January 2012.
7. Bouza, E. Clin. Microbial Infect. 18 (suppl. 6): 5, 2012
8. Khanna, S. and pardi D. S. Mayo Clin Proc. 87: 1106, 2012.
9. Johnson, S. et al. Antimicrobial Agents & Chemotherapy 56: 4043, 2012
10. Ananthakrishnan A. N. Gastroenterol Hepatol. 8: 17, 2011
11. Sanchez-K. et al. J. Med. Microbial. 57:717, 2008.
12. Lowy, I. et al. N Engl. J Med. 362:197, 2010.
13. Basseri, R. J. et al. Gastroenterol. Hepatol. 7: 455, 2011
14. Hulisz, D. J. Manag Care Pharm 10: 299, 2004
15. Furnari, M. et al. J Gastrointestin Liver Dis. 21: 157, 2012.
16. Hanada et al., 2017, Clin Gastro Hepatol. Nov. 24, 2017
17. D'aoust et al., 2017, World J Gastro 23: 4986-5003.
18. Nitzan et al., 2013, World J Gastro 19: 7577-7585.
19. Binion, 2016, Gastro & Hepatol. 12: 334-337.
20. Odes, S L et al 2011, Annals Gastroenterology 24: 263-270.
21. Rodemann J F et al. 2007. Clin. Gastroenterol. Hepatol. 5:339-344.

The invention claimed is:

1. A method for treating or prophylactically treating Inflammatory Bowel Disease or a flare of Inflammatory Bowel Disease associated with *Clostridium difficile* by administering an effective amount of a polyclonal antibody composition to an individual in need of such treatment,
   wherein said individual is an individual suffering from or previously diagnosed with an Inflammatory Bowel Disease and is infected with *C. difficile*; and
   wherein said polyclonal antibody composition is prepared by:
   a) immunizing a first group of egg-laying hens with an antigen prepared from *Clostridium difficile* Toxin A;
   b) immunizing a second group of egg-laying hens with an antigen prepared from *Clostridium difficile* Toxin B;
   c) immunizing a third group of egg-laying hens with an antigen prepared from *Clostridium difficile* spores;
   d) collecting eggs laid by said first group, said second group and said third group; and
   e) recovering polyclonal antibodies from said collected eggs.

2. The method according to claim 1, wherein the antigens are administered to the hens in combination with an adjuvant.

3. The method according to claim 2 wherein the adjuvant is MONTANIDE-ISA-70™ (mineral based oil adjuvant).

4. The method according to claim 1 wherein the polyclonal antibodies are recovered from the collected eggs by freeze-drying.

5. The method according to claim 1 wherein the polyclonal antibodies are recovered from the collected eggs by spray-drying.

6. The method according to claim 1 wherein the polyclonal antibody composition has a reciprocal titer of <128,000.

7. The method according to claim 1 wherein the polyclonal antibody composition is administered until severity of symptoms of the *Clostridium difficile* infection has been reduced.

8. The method according to claim 1 wherein the effective amount is between about 2-40 g.

9. The method according to claim 1 wherein the effective amount is between about 5-30 g.

10. The method according to claim 1 wherein the effective amount is between about 5-20 g.

11. The method according to claim 1 wherein the polyclonal antibody composition is administered daily for a period of at least 7 days.

12. The method according to claim 1 wherein the polyclonal antibody composition is administered daily for a period of at least 10 days.

13. The method according to claim 1 wherein the polyclonal antibody composition is administered daily for a period of about 7-21 days.

14. The method according to claim 1 wherein the polyclonal antibody composition is administered daily for a period of about 10-14 days.

15. The method according to claim 1 wherein the polyclonal antibodies are purified from the collected eggs.

16. The method according to claim 1 wherein the polyclonal antibody composition is administered orally.

17. The method according to claim 1 wherein the individual is an asymptomatic carrier of *C. difficile*.

18. The method according to claim 1 wherein the polyclonal antibody composition is administered in the absence of coadministration of corticosteroids or other immunosuppressive agents.

* * * * *